US010792258B2

(12) United States Patent
Magaña Castro et al.

(10) Patent No.: US 10,792,258 B2
(45) Date of Patent: Oct. 6, 2020

(54) ANTISEPTIC, ANTISEBORRHEIC AND EXFOLIATING COMPOSITION TO REMOVE OR PREVENT ACNE

(71) Applicant: Excalibur Pharmaceuticals, Inc., New York, NY (US)

(72) Inventors: José Agustín Rogelio Magaña Castro, Mexico City (MX); Laura Vázquez Cervantes, Mexico City (MX); Pedro Peña Santoyo, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/371,670

(22) Filed: Apr. 1, 2019

(65) Prior Publication Data

US 2019/0290606 A1    Sep. 26, 2019

Related U.S. Application Data

(63) Continuation of application No. 16/008,210, filed on Jun. 14, 2018, now abandoned, which is a continuation of application No. 14/421,616, filed as application No. PCT/MX2013/000099 on Aug. 22, 2013, now abandoned.

(30) Foreign Application Priority Data

Aug. 23, 2012   (MX) ................... MX/A/2012/009806

(51) Int. Cl.
| | |
|---|---|
| *A61K 31/191* | (2006.01) |
| *A61Q 17/00* | (2006.01) |
| *A61Q 19/10* | (2006.01) |
| *A61Q 19/00* | (2006.01) |
| *A61K 31/10* | (2006.01) |
| *A61K 8/46* | (2006.01) |
| *A61K 8/365* | (2006.01) |

(52) U.S. Cl.
CPC ............ *A61K 31/191* (2013.01); *A61K 8/365* (2013.01); *A61K 8/46* (2013.01); *A61K 31/10* (2013.01); *A61Q 17/005* (2013.01); *A61Q 19/008* (2013.01); *A61Q 19/10* (2013.01); *A61K 2800/28* (2013.01)

(58) Field of Classification Search
None
See application file for complete search history.

(56) References Cited

U.S. PATENT DOCUMENTS

| | | | |
|---|---|---|---|
| 4,105,782 A | 8/1978 | Yu et al. | |
| 4,376,118 A | 3/1983 | Daher et al. | |
| 5,009,895 A | 4/1991 | Lui | |
| 5,811,130 A | 9/1998 | Boettner et al. | |
| 5,958,420 A | 9/1999 | Jenson | |
| 6,365,131 B1 | 4/2002 | Doshi et al. | |
| 7,109,246 B1 | 9/2006 | Hawtin | |
| 8,492,412 B2 | 7/2013 | Magana Castro et al. | |
| 9,408,836 B2 | 8/2016 | Armendariz Borunda et al. | |
| 9,949,959 B2 | 4/2018 | Armendariz Borunda et al. | |
| 9,962,374 B2 | 5/2018 | Armendariz Borunda et al. | |
| 10,376,500 B2 | 8/2019 | Magana Castro et al. | |
| 10,383,862 B2 | 8/2019 | Armendariz Borunda et al. | |
| 2004/0029946 A1 | 2/2004 | Arora et al. | |
| 2004/0235946 A1 | 11/2004 | Ott | |
| 2006/0051339 A1 | 3/2006 | Sivak | |
| 2006/0115503 A1 | 6/2006 | Goyal | |
| 2008/0319026 A1 | 12/2008 | Gant et al. | |
| 2011/0224265 A1 | 9/2011 | Magana Castro et al. | |
| 2013/0245073 A1 | 9/2013 | Magana Castro et al. | |
| 2014/0296300 A1 | 10/2014 | Armendariz Borunda et al. | |
| 2015/0148382 A1 | 5/2015 | Armendariz Borunda et al. | |
| 2015/0231098 A1 | 8/2015 | Magana Castro et al. | |
| 2016/0228424 A1 | 8/2016 | Armendariz Borunda et al. | |
| 2016/0287567 A1 | 10/2016 | Armend Riz Borunda et al. | |
| 2017/0216268 A1 | 8/2017 | Magana Castro et al. | |
| 2018/0092893 A1 | 4/2018 | Armend Riz Borunda et al. | |
| 2018/0214434 A1 | 8/2018 | Armend Riz Borunda et al. | |
| 2018/0353448 A1 | 12/2018 | Magana Castro et al. | |
| 2019/0262325 A1 | 8/2019 | Armend Riz Borunda et al. | |
| 2019/0358213 A1 | 11/2019 | Armend Riz Borunda et al. | |

FOREIGN PATENT DOCUMENTS

| | | |
|---|---|---|
| CN | 101972236 | 2/2011 |
| CN | 101972236 A | 2/2011 |
| EP | 1356816 A1 | 10/2003 |

(Continued)

OTHER PUBLICATIONS

Allicinnow, "allicin," retrieved online at: http://www.allicinnow.com/allicin/acne-treatment/, 2 pages (2010).

(Continued)

*Primary Examiner* — Erin E Hirt

(74) *Attorney, Agent, or Firm* — Wolf, Greenfield & Sacks, P.C.

(57) ABSTRACT

The invention refers to an antimicrobial, exfoliating and seboregulating hydrosoluble composition comprising a combination of diallyl disulphide modified oxide (DDMO) and alpha hydroxyethanoic acid (glycolic acid), which acts removing bacteria affecting the skin including those caused by acne, said composition also provides deep cleansing, exfoliating action, reduces epidermal cohesion facilitating cellular change, preventing the occurrence of several forms of acne in the skin and additionally producing seboregulating effects by avoiding blockage of sebaceous glands.

16 Claims, No Drawings

(56) References Cited

FOREIGN PATENT DOCUMENTS

| | | | |
|---|---|---|---|
| EP | 2177220 A1 | 4/2010 |
| MX | 2013008151 A | 10/2013 |
| WO | 2000/16775 A1 | 3/2000 |
| WO | 0016775 A1 | 3/2000 |
| WO | 2004/073713 A1 | 9/2004 |
| WO | 2007/038315 A2 | 4/2007 |
| WO | 2008107873 A1 | 9/2008 |
| WO | 2009/022899 A1 | 2/2009 |
| WO | 2013/012307 A1 | 1/2013 |
| WO | 2013/147577 A1 | 10/2013 |

OTHER PUBLICATIONS

Armendariz-Borunda, Juan et al., "A Controlled Clinical Trial With Pirfenidone in the Treatment of Pathological Skin Scarring Caused by Burns in Pediatric Patients," Annals of Plastic Surgery, vol. 68(1):22-28 (2012).
Gad, C.G., "Pharmaceutical Manufacturing Handbook: production and processes," John Wiley & Sons, ISBN: 978-0-470-25958-0, 1386 pages (Mar. 2008).
International Preliminary Report on Patentability for Application No. PCT/MX2008/000107, 5 pages, dated Dec. 1, 2009.
International Preliminary Report on Patentability for Application No. PCT/MX2012/000067, 8 pages, dated Aug. 7, 2013.
International Preliminary Report on Patentability, PCT/MX2013/000099, dated Dec. 19, 2014, pp. 1-7.
International Search Report and Written Opinion for Application No. PCT/MX2012/000067, dated Nov. 22, 2012, 14 pages.
International Search Report and Written Opinion for Application No. PCT/MX2013/000027, 11 pages, dated Jun. 5, 2013.
International Search Report for PCT/MX2008/000107, dated Dec. 9, 2008, 4 pages.
International Search Report, PCT/MX2013/000099, dated Aug. 8, 2014, pp. 1-5.
International Search Report, PCT/MX2013/000099, dated Aug. 8, 2014, pp. 5.
Josling, Peter, "Peter Josling's PowerPoint on AllicinCenter Products and Their Uses," retrieved from the internet at: http://allicincenter.com/reference.php?id=products, 15 pages (2013).
Tiwari, S., et al., "Applications of Complementary Polymers in HPMC Hydrophilic Extended Release Matrices," Drug Delivery Technology, Formulating Hydrophilic Matrix Systems, vol. 9(7), 7 pages (2009).
U.S. Appl. No. 16/008,210, filed Jun. 14, 2018, José Agustín Rogelio Magaña Castro.
U.S. Appl. No. 14/421,616, filed Feb. 13, 2015, José Agustín Rogelio Magaña Castro.
U.S. Appl. No. 16/450,150, filed Jun. 24, 2019, José Agustín Rogelio Magaña Castro.
U.S. Appl. No. 15/435,494, filed Feb. 17, 2017, José Agustín Rogelio Magaña Castro.
U.S. Appl. No. 13/893,626, filed May 14, 2013, José Agustín Rogelio Magaña Castro.
U.S. Appl. No. 12/673,304, filed Apr. 28, 2010, José Agustín Rogelio Magaña Castro.
U.S. Appl. No. 15/831,650, filed Dec. 5, 2017, Juan Armendáriz Borunda.
U.S. Appl. No. 15/177,760, filed Jun. 9, 2016, Juan Armendáriz Borunda.
U.S. Appl. No. 14/233,600, filed May 20, 2014, Juan Armendáriz Borunda.
U.S. Appl. No. 15/920,822, filed Mar. 14, 2018, Juan Socorro Armendáriz Borunda.
U.S. Appl. No. 15/098,970, filed Apr. 14, 2016, Juan Armendáriz Borunda.
U.S. Appl. No. 14/388,447, filed Feb. 5, 2015, Juan Armendáriz Borunda.
U.S. Appl. No. 16/008,210, Oct. 1, 2018.
U.S. Appl. No. 14/421,616, Dec. 14, 2017.
U.S. Appl. No. 14/421,616, Mar. 6, 2017.
U.S. Appl. No. 14/421,616, May 19, 2016.
U.S. Appl. No. 14/421,616, Nov. 9, 2015.
U.S. Appl. No. 15/435,494, Apr. 3, 2019.
U.S. Appl. No. 15/435,494, Sep. 20, 2018.
U.S. Appl. No. 15/435,494, Jan. 26, 2018.
U.S. Appl. No. 15/435,494, Sep. 8, 2017.
U.S. Appl. No. 13/893,626, Aug. 22, 2016.
U.S. Appl. No. 13/893,626, Dec. 17, 2015.
U.S. Appl. No. 13/893,626, Apr. 14, 2015.
U.S. Appl. No. 12/673,304, Mar. 8, 2013.
U.S. Appl. No. 12/673,304, Jun. 20, 2012.
U.S. Appl. No. 12/673,304, Mar. 14, 2012.
U.S. Appl. No. 15/831,650, Jun. 26, 2019.
U.S. Appl. No. 15/831,650, Mar. 19, 2019.
U.S. Appl. No. 15/831,650, Oct. 12, 2018.
U.S. Appl. No. 15/831,650, Jun. 13, 2018.
U.S. Appl. No. 15/177,760, Jan. 24, 2018.
U.S. Appl. No. 15/177,760, Apr. 17, 2017.
U.S. Appl. No. 15/177,760, Dec. 15, 2016.
U.S. Appl. No. 14/233,600, Jun. 14, 2016.
U.S. Appl. No. 12/233,600, Nov. 23, 2015.
U.S. Appl. No. 14/233,600, Jul. 8, 2015.
U.S. Appl. No. 15/920,822, Feb. 7, 2019.
U.S. Appl. No. 15/920,822, Nov. 15, 2018.
U.S. Appl. No. 15/098,970, Dec. 15, 2017.
U.S. Appl. No. 15/098,970, Mar. 23, 2017.
U.S. Appl. No. 15/098,970, Jan. 11, 2017.
U.S. Appl. No. 14/388,447, Oct. 15, 2015.
U.S. Appl. No. 16/348,189, filed May 8, 2019, Juan Socorro Armendáriz Borunda.
U.S. Appl. No. 16/450,150, filed Jun. 24, 2019, José Agustín Rogelio Magaña Castro.
U.S. Appl. No. 16/460,407, filed Jul. 2, 2019, Juan Armendáriz Borunda.
U.S. Appl. No. 16/534,980, filed Aug. 7, 2019, Juan Socorro Armendariz Borunda.
U.S. Appl. No. 16/450,150, Nov. 1, 2019.

ANTISEPTIC, ANTISEBORRHEIC AND EXFOLIATING COMPOSITION TO REMOVE OR PREVENT ACNE

RELATED APPLICATIONS

This application is a continuation of U.S. application Ser. No. 16/008,210, filed on Jun. 14, 2018, which is a continuation of U.S. application Ser. No. 14/421,616, filed on Feb. 13, 2015, which is a 35 U.S.C. 371 National Stage Filing of International Application No. PCT/MX2013/000099, filed on Aug. 22, 2013, which claims priority to Mexican Application No. MX/A/2012/009806, filed on Aug. 23, 2012. The contents of the aforementioned applications are hereby incorporated by reference in their entireties.

FIELD OF THE INVENTION

The present invention relates to a hydrosoluble pharmaceutical antiseptic, antiseborrheic and exfoliating composition comprising a combination of diallyl disulphide modified oxide (DDMO) and alpha hydroxyethanoic acid (glycolic acid) to remove bacteria affecting the skin, besides said composition provides a deep cleansing because it reduces the epidermal cohesion and facilitates the cellular replacement, preventing or removing the occurrence of several forms of alterations in the skin.

BACKGROUND OF THE INVENTION

The skin has a microbial flora, which can be affected by changes in normal conditions of the skin, more likely acne is the most frequency of these alterations, due to the multiple factors altering it and producing a balance loss of the microbial flora.

Acne is an inflammatory illness of the pilosebaceous follicles, associated to the keratinization and seborrhea alterations; characterized by the formation of skin wounds such as: blackheads, papulae, pustules, cysts or abscesses, which frequently leave residual scars.

Acne is undoubtedly the most frequent skin disease in the entire world; traditionally the three main factors considered to intervene in the appearance of acne were microbial infection, overproduction of fat and abnormal peeling of epidermal cells that finally cause an excess in the keratinization, but recent studies add as causing effects of acne genetic predisposition and inflammatory factor.

It is calculated that about 85% of the population between the ages of 11 and 30 suffer from acne; this represents only in Mexico an approximate total of 20 million people. The incidence curves show a maximum peak at 18 years old, from this point a gradual decrease is appreciated, which increases after 30 years of age; however, between 25 and 35% of adults over 35 years old go through occasional acne exacerbations.

The cause of acne is precisely unknown, due to the fact that a great amount of factors jointly intervene, however, among them it is worth mentioning the genetic factor, which in combination with the endocrinal, inflammatory and infectious factors, are somehow the cause of the polymorphic characteristic of acne.

There are 5 main primary pathogenic factors interacting in a complex manner to produce acne injuries.
1. Genetic predisposition.
2. Overproduction of fat by sebaceous glands.
3. Alteration in the keratinization process with abnormal peeling of the sebaceous follicular epithelium (causing comedogenesis).
4. Proliferation of *Propionibacterium acnes*.
5. Release of inflammatory intermediaries on the skin, mainly alpha-TNF and alpha IL-1.

The genetic predisposition is not mediated by one simple Mendelian character, but it is caused by an intermediary of a polygenic mechanism, which originates special receptiveness of the pilosebaceous follicle, in order to more intensely responds to androgens, different from how healthy people respond.

Research made about the role of fat in acne has allowed to establishing that the sebaceous lipids are regulated by the peroxisome proliferator activated-receptors (PPAR) and by sterol transcription factors.

Other research of the sebaceous gland function has contributed to obtaining information about the main role these glands play in regulating skin functions. The sebaceous gland has direct and indirect antibacterial activities. Likewise, the sebaceous gland produces antibacterial peptides and proinflammatory cytokines that are induced in sebocytes due to the presence of bacteria.

Androgens are hormones synthesized in testicles, ovaries and suprarenal cortex. During puberty, through little known mechanisms, the hypophysis starts to secrete greater amounts of luteinizing hormones (HL) and follicle-stimulating hormones (FSH), which together are responsible for the increase in testicular growth, spermatogenesis, and steroidogenesis. Testosterone acts upon sebaceous glands, increasing their size and fat synthesis; in women the mechanism is similar. Through biopsies to the face skin in patients with acne, it has been proven that during puberty the sebaceous glands are bigger and foliated.

Some time ago it was believed that acne was just an infectious process caused by the bacteria "*Acne bacillus*", now called *Propionibacterium acnes*. The cutaneous flora is essentially a triad lead by the *Propionibacterium acnes*, in addition to *Staphylococcus epidermis* and yeast, which can be *Pityrosporum ovale* or *Pityrosporum orbiculare*.

It is possible that the association between bacteria and the pathogenesis of the acne is reinforced by well-documented findings about clinical improvement in patients with acne treated with systemic antibiotics. The antibacterial therapy does not affect the *P. orbiculare* or *P. ovale* since they reside on the upper part of the acrofundibulum of the sebaceous follicle. The anaerobe *P. acnes* on the other hand seems to play a central role in the development of acne inflammation. The most important evidence might be the demonstration that therapy with antibiotics results in a significant suppression of *P. acnes*, which is accompanied in one reduction in the number of inflammatory injuries.

*Propionibacterium acnes* and *Staphylococcus epidermidis* are produces of a lipase that hydrolyzes triglycerides from fat in fat-free acids, which are potent irritants from the follicular channel, when applied on the skin or intradermally injected, they cause inflammation and blackheads.

It must also be noted that the *Propionibacterium acnes* alternately activates the complement system, this fact has allowed to propose that this infectious mechanism could also play an important role in the production of acne inflammatory injuries.

During puberty, and in response to the androgens produced in greater amounts in this stage, the sebaceous glands that were relatively inactive, increase in size and become more foliated, thus increasing the production of fat spilled on the outside; thereby the first sign of acne: seborrhea.

The recently synthesized fat contains triglycerides, squalene and wax esters, and it is known that *Propionibacterium acnes* through a lipase hydrolyzes triglycerides from this sebaceous material, thus converting them into fat free acids, which in addition to other irritant substances as squalene and oleic acid cause inflammation of the follicular channel, which responds to the inflammation with hyperkeratosis. The resulting corneous material fall in the light of the follicle, which in addition to the fat excess forms wax substituting and easing the follicle walls, accordingly by not being able to excrete material, it inflames more, causing the first and most important acne elemental injury: the blackhead, causing dilation of the follicular hole due to the pressure the wax applies when trying to be expelled.

In several studies, it was been studied in depth the role of the inflammatory mediators, as well as the interrelation of this factor with sebaceous lipids and matrix metaloproteinases (MMP's) in the physiology of acne.

One of the pioneer researches in this field was developed by Jeremy and co-workers in 2003, who researched the initial events of acne injuries and found that the immunological changes and inflammatory responses occurred before the hyperproliferation of keratinocytes, with a similar pattern to a type IV retarded hypersensitivity. An important fact is that the whole process starts by the exacerbated regulation of IL1-β having a proinflammatory action in response to the linoleic acid relative deficiency caused by the fat excess and by the disturbance of the barrier function inside the follicle. Vowels and co-workers proved in an in vitro study the presence of a *P. acnes* soluble factor that also induces the production of pro-inflammatory cytokines in cellular lines derived from human monocytes. This product of *P. acnes* induces the synthesis of the alpha tumor necrosis factor (α-TNF) and interleucine 1-beta (IL1-β) in said cellular lines. It was also shown that the induction of cytokines by *P. acnes* would happen through the activation of the "TOLL-LIKE-2" Receptor (TLR-2) shooting inflammatory responses.

Other recent studies have proved that this chain of events occurs in inflammatory injuries from patients with facial acne. It has been shown that the *Propionibacterium acnes* also induces type Toll receptors. This provides additional evidence that the inflammatory cytokines, which act through autocrine and paracrine mechanisms amplifying their corresponding receptors and amplifying the signaling way that activates the Activator Protein-1 (AP-1) that is a transcriptional factor.

In treating acne, the use of antimicrobials is a normal and habitual behavior among doctors, since there is clinically an improvement in patients with acne when using this type of products, this due to the strengthening factor of *P. acnes* in the fat metabolism that creates an irritant effect causing greater inflammation on the patient.

The diallyl disulphide oxide (DDO) is also known as allicin, is the product from the conversion of allina, which is found in garlic (*Allium sativum*), by means of allinase enzyme catalysis. It is a sulfurated compound containing diverse pharmacological activities of interest. The DDO is not naturally found in garlic, but when the bulb fractures, it is cut or grinded, liberates allina, which when contacting the allinase enzyme creates the active principle. Allina is found in amounts varying from 0.22-0.24% by weight of garlic and is an amino acid that is it not a structural part of any protein and it is not biochemically essential for human nutrition.

Since it is a not much stable compound, the DDO quickly loses its properties, on the other hand if garlic is heated over 60° C. it loses its properties. It has a strong oxidative power that could cause harm to intestinal cells.

It has been shown that DDO has in vitro activity against *Candida albicans*, some *Trichomonas*, *Staphylococcus aureus*; *Escherichia coli*, *Salmonella typhi*, *S. paratyphi*, *Shigella dysenterica* and *Vibro cholera* species.

The structural formula of allicin is shown below:

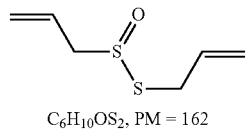

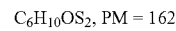

$C_6H_{10}OS_2$, PM = 162

In 1944 Cavallito and his co-workers were able to isolate and identify the active compound from the extracts of *Allium sativum* which they called allicin and in 1947 they were able to synthesize the diallyl disulphide oxide (allicin), but unfortunately they were not able to make the molecule thereof stable, since it kept losing its efficacy in a very short period of time. A group of Mexican researchers from 2000 and 2005 were able to stabilize the diallyl disulphide oxide, adding a co-factor, compound called diallyl disulphide modified oxide [DDMO], which is much more stable than allicin and it seems to maintain its properties.

The diallyl disulphide modified oxide [DDMO], is the chemical compound called [1,2-alpha-glucodiallyl-disulphide oxide, 2-propen+chloride-6 alkyl (benzyl, methyl, octyl ammonium-hydroxymethylamine); whose structural formula is represented as follows:

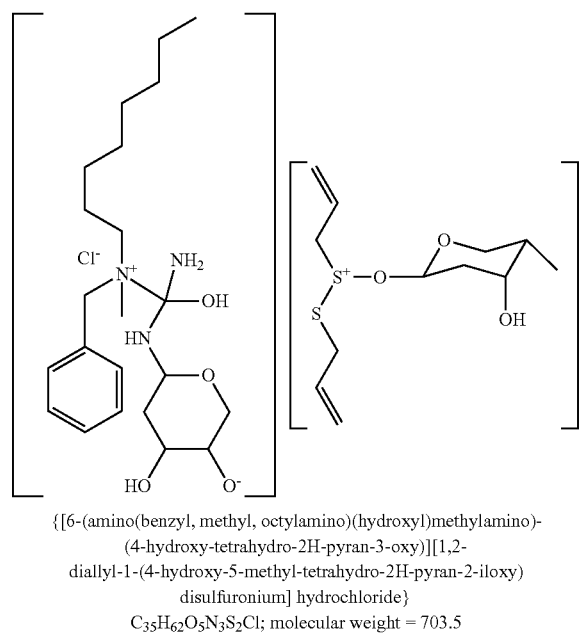

{[6-(amino(benzyl, methyl, octylamino)(hydroxyl)methylamino)-
(4-hydroxy-tetrahydro-2H-pyran-3-oxy)][1,2-
diallyl-1-(4-hydroxy-5-methyl-tetrahydro-2H-pyran-2-iloxy)
disulfuronium] hydrochloride}
$C_{35}H_{62}O_5N_3S_2Cl$; molecular weight = 703.5

In diverse studies it has been shown the activity of allicin, however its little stability has been a limitation in its possible therapeutic applications. Accordingly, it is clear that the application of the stability properties of compound DDMO, will allow the therapeutic application based on its antibacterial and anti-septic properties among others from allicin.

On the other hand, hydroxyethanoic acid (HAA), is also called glycolic acid, which is an acid of small molecular chain having the ability to penetrate the skin faster that deeper layers. It is shown colorless, odorless, and hygroscopic crystalline solid that is highly water-soluble and in related solvents. This acid is largely used in dermatologic treatments, there are studies demonstrating its efficacy, through methods such as computerized morphometry on corneal layers from biopsies. Normally it is employed in association with other dermatologic products supporting the cellular reconstruction of the skin, thus becoming the so-called "soft-peeling" base. The treatment action with hydroxyethanoic acid is to decrease the corneal layer thickness of the skin and to increase the malpighian layer thickness; the fractions of areas occupied by collagen in dermal layers significantly increases, thereby there is an improvement in the appearance of atrophic scars from acne and in the treatment of human skin wrinkles. It is also an excellent exfoliator, thus helping to significantly prevent and combat acne in any body part. The glycolic acid also lets other components to more easily penetrate the skin, thus it is advisable to also use the so-called complete treatments. The hydroxic acid also has seboregulating properties by increasing the peeling of cells and thus avoiding blockage of the sebaceous glands and the formation of blackheads and other acne injuries.

OBJECT OF THE INVENTION

A first object of the present invention is to provide antimicrobial, exfoliating and seboregulating pharmaceutical hydrosoluble compositions comprising a combination of diallyl disulphide modified oxide (DDMO) and alpha-hydroxyethanoic acid (glycolic acid) to remove or prevent acne.

A second object is to obtain compositions comprising a combination of diallyl disulphide modified oxide (DDMO) and alpha-hydroxyethanoic acid (glycolic acid), antimicrobials/antiseptics, stable, biodegradable and non-poisonous topical application exfoliants and seboregulators having as an antimicrobial function a wide action spectrum, not just against gram negative and gram positive microorganisms, but against fungus as well.

The previous objects are representative, but they shall not be considered as limitative to the present invention, wherein it is further shown its treatment methods, applications and/or pharmaceutical uses in the preparation of medicaments to remove, reduce or prevent microbial injuries of the skin, including acne.

DESCRIPTION OF THE INVENTION

The present invention is related to antimicrobial, exfoliating and seboregulating pharmaceutical hydrosoluble compositions comprising from 0.001 to 10% p/w of the DDMO composition, from 1 to 12% p/w of alpha-hydroxyethanoic acid (glycolic acid), from 0.3 to 24% p/w of one or more surfactants, from 0.3 to 10% p/w of a moisturizing agent, from 0.2 to 10% p/w of an aromatizing agent and from 40 to 70% p/w of the composition of an aqueous solvent.

Particularly, the object compositions of the present invention comprise one or more surfactants selected from the group consisting of lineal alkyl benzene sulfates and ionic alkyl sulfates.

The surfactants useful in the object compositions of the present invention preferably are sodium lauryl sulfate and sodium lauryl ether sulfate.

The ionic alkyl surfactants, such as sodium lauryl sulfate that is an anionic surfactant, are used in a variety of pharmaceutical non-parenteral formulations. For example, the sodium lauryl sulfate is a detergent and moisturizing agent, effective in acid, alkaline solutions and in hard water. It is used in medicated shampoos, such as skin cleaner and dentifrices, it is usually known as "Cosmetic Detergent", makes foam and bubbles and is good for removing grease and oil from skin and hair.

Likewise, the sodium lauryl ether sulfate is the most frequently used active anion surfactant in the manufacture of cleaning, scrubbing and domestic washing products, as well as cosmetic and personal hygiene products. The sodium lauryl ether sulfate does not irritate the skin and if from natural origin; additionally it is valued for its easy degradations and properties in relation to the formation of foam. The sodium lauryl ether sulfate is mainly used in the production process of shampoos, liquid soaps, face skin creams, dental creams, etc.

The surfactant preferably used in the present invention are sodium lauryl sulfate, sodium lauryl ether sulfate and ammonium lauryl sulfate.

The moisturizing agent is selected from the group consisting of ethylene glycol, propylene glycol, glycerin, sorbitol, low molecular weight polyethylenes, polyoxyethylated glycerols, polyoxyethylated sugars, for example, MEA acetamide, and the like. Preferably, the moisturizing agent is glycerin, which has a wide variety of applications, such as emulsifier, softening agent, laminate, stabilizing and moisturizing agent for baking shop, ice-cream shop and cigar store, in body lotions, mouthwashes, as protecting means for freezing of red blood cells, sperm, corneas and other tissues in printing inks, paint resins; antifreezing mixtures; and as raw material for nitroglycerin. It is used in the manufacture of countless prepared pharmaceuticals and cosmetics; for example in soaps, glycerin increases its detergency, whitening and softening of the skin. Between 8-15% of glycerin can be found in the compositions of these soaps.

Other moisturizing agents useful in the compositions claimed in the present invention comprise among others:

A aromatizing agent selected from any of the available ones for the pharmaceutical and food industry.

An aqueous solvent, which is selected from water and water-hydrosoluble alcohol mixtures.

With these elements, it is possible to extract a wide range of antimicrobial, exfoliating and seboregulating pharmaceutical compositions containing DDMO and alpha-hydroxyethanoic acid (glycolic acid), useful in treating and preventing skin microbial injuries.

Said compositions contribute to eliminate bacteria causing acne providing a deep and delicate cleansing of the skin; even in oily skins, improving the habitual look and freshness. In addition to its antimicrobial action, it provides an exfoliating action, reducing the epidermal adhesion and facilitating the cellular change, eliminating dead skin cells. Also, they remove the grease and oil excess present in the acne skin, thus preventing obstruction of the pores, removing comedonal block and avoiding formation of new blackheads and pustules.

The information obtained from microbiologic tests (antimicrobial challenge) of the DDMO and alpha-hydroxyethanoic acid (glycolic acid) against several bacteria, has proven the great antibacterial capacity of the formulations, insisting on the results against *Propionibacterium acnes*, thus proving the removal of said bacteria in a matter of seconds.

The antimicrobial action mechanism of DDMO, probably comprises the following:

1. Alteration of the microbial mechanism, inhibiting the action of 11 essential enzymes for cellular respiration of the microorganism. This inhibiting effect is created from the chemical reaction of the sulfhydryl radicals of DDMO about the molecular structure of the sulfurated enzymes of the microorganism, whether by inserting sulfurated radicals or by modifying the enzyme protein, thus causing death of the microorganism.

2. Through reactions of oxide-reduction creating free radicals (ROS), which by oxidative stress break the cellular wall of the microorganism, by acting "sequestering" oxygen serving as link between the NAG (n-Acetyl glucosamine acid) and NAM (N-Acetyl muramic acid) chains, thus weakening the microorganism wall causing rupture and thereby death of the microorganism.

3. Inhibition of the genetic transcription process and unfolding of the microorganism proteins, through the activation of the polymerase ARN enzyme, which is an enzyme, since being of sulfurated composition, is vulnerable to chemical attack from the DDMO.

4. Alteration of the metal metabolism in the microorganism, also causing metabolic alterations therein.

The foregoing has been inferred from studies made with allicin, reported by Yosuda et al, Biosci. Biotechnol. Biochem., 63(3) 591-594, 1999; Feldherg et al, Antimicrobial Agents and Chemotherapy, December 1988, 1763-1768; Münchberg et al, Org. Biomol. Chem., 2007, 5, 1505-1518; among others. Considering that DDMO is an stabilized allicin molecule owing its antimicrobial action precisely to this allicin fragment, whose activity is preserved without alteration as shown in the microbiological tests.

The microbiological challenges were made with collection microorganisms, universally required to test the product effectiveness. The results proved that in 30 seconds of contact with the composition from Example 1, 100.00% was removed from the challenged microorganisms, including *Candida albicans*. The results from the study are shown in Table 1.

TABLE 1

Studies from microbial challenge

| Test Microorganism | Contact Time 30 Sec |
|---|---|
| *Escherichia coli* ATCC 10536 | 100% |
| *Pseudomona aerugiosa* ATCC 9027 | 100% |
| *Klebsiellapneumoniae* ATCC 10031 | 100% |
| *Proteus vulgaris* ATCC 6380 | 100% |
| *Staphylococcus aureus* ATCC 6538 | 100% |
| *Staphylococcus epidermis* ATCC 12228 | 100% |
| *Candida albicans* ATCC 1031 | 100% |

Additionally, challenge tests were made against *Propionilbacterium acnes*, anaerobic bacteria previously referred to as one of the main causes of infection caused by acne, thus obtaining excellent results, such as it is shown below in Table 2.

TABLE 2

| Test Microorganism | Contact Time 30 seconds | Eradication 60 seconds |
|---|---|---|
| *Propionibacterium acnes* | 98% | 99.999% |

The results of these microbial challenges are more encouraging that those reported by Fujisawa et al, Biosci. Biotechnol. Biochem. 73 (9) 1984-1955, 2009; Tsao et al Journal of Medical Microbiology (2007) 56, 803-808. And they confirm the review by Ankri and Mirelman, Microbes and Infection, 2, 1999, 125-129 and by Domingo and Lopez-Brea in Rev. Esp. Quimioterap. December 2003, Vol. 16 (no. 4) 285-293 (2003).

Example 1

An antimicrobial and antiseptic hydrosoluble composition was prepared containing:

| Component | Kg |
|---|---|
| a-hydroxyethanoic acid | 57.1 |
| DDMO | 4 |
| Sodium lauryl sulfate | 50 |
| Sodium lauryl ether sulfate | 50 |
| Glycerin | 2.5 |
| Blue fragrance | 3 |
| Purified water | 333.4 |

Example 2

A second composition was prepared containing the following elements:

| Component | Kg |
|---|---|
| a-hydroxyethanoic acid | 58 |
| DDMO | 5 |
| Sodium lauryl sulfate | 40 |
| Sodium lauryl ether sulfate | 60 |
| Ethylene glycol | 2.5 |
| Floral fragrance | 3 |
| Purified water | 331.5 |

Example 3

A third example of the object compositions of the present invention is shown, thus proving that the embodiments of the same only limit to preserving the homogeneous distribution aspects of all components.

| Component | Kg |
|---|---|
| a-hydroxyethanoic acid | 57.1 |
| DDMO | 4 |
| Sodium lauryl ether sulfate | 100 |
| Sorbitol | 2 |
| Blue fragrance | 3 |
| Purified water-ethanol (9:1) | 333.9 |

Clinical Trials:

A clinical trial was made applying the product of the present invention (example 1) during 28 days to 20 patients with moderate acne, according to the classification shown in Table 3 below.

TABLE 3

| Grade* | Description |
|---|---|
| 0 | Clean skin with no inflammatory or non-inflammatory wounds |
| 1 | Almost clean; Little non-inflammatory wounds and no more tan two inflammatory wounds |
| 2 | Middle severity; greater than grade 1; some non-inflammatory wounds, few inflammatory wounds (only papules/pustules; no nodular wounds) |
| 3 | Moderate severity; greater than grade 2; many non-inflammatory wounds and several can be inflammatory, but no more than two nodular wounds. |
| 4 | Severe; greater than grade 3; many inflammatory and non-inflammatory wounds; and some nodular wounds. |

❖FDA's classification scale of acne

The number of wounds from each patient was counted by two different observers before treatment and during the same each week. The resulting data is shown in table 4, wherein it can be seen that the treatment gave an average reduction close to 35% of the active wounds after 28 days of treatment.

TABLE 4

| | No. Of Inflammatory Wounds | | | | |
|---|---|---|---|---|---|
| Number | Day 0 | 7 days | 14 days | 21 days | 28 days |
| 1 | 58 +/− 5 | 51 +/− 5 | 45 +/− 4 | 41 +/− 3 | 37 +/− 3 |

On the other hand, patients were asked to assess the presence of grease, through the use of drying paper, measuring the number of sheets needed in order not to get the forehead stained 2 hours after cleaning with the product, thus discovering that patients considerably reduced the number of drying sheets used for cleaning the grease, the results are shown in Table 5.

TABLE 5

| No. Of Sheets | | | | |
|---|---|---|---|---|
| Day 0 | 7 days | 14 days | 21 days | 28 days |
| 5 +/− 2 | 2 +/− 2 | 1 +/− 2 | 1 +/− 1 | 1 +/− 1 |

The results show that the antiseptic, antiseborrheic and exfoliating composition of the present invention is able to achieve an effective treatment for seborrhea and acne. These results show that the treatment for these disorders according to the present invention is clearly better than the pre-existing methods.

The invention claimed is:

1. A hydrosoluble, topical pharmaceutical composition comprising from 0.001 to 10% by weight of diallyl disulfide modified oxide, from 1 to 12% by weight of glycolic acid, from 0.3 to 24% by weight of one or more surfactants, from 0.3 to 10% by weight of a moisturizing agent, from 0.2 to 10% by weight of an aromatizing agent, and from 40 to 70% by weight of an aqueous solvent.

2. The composition according to claim 1, wherein the surfactants are selected from the group consisting of linear alkylbenzensulfonates and ionic alkyl sulfates.

3. The composition according to claim 1, wherein the surfactants are selected from the group consisting of sodium lauryl sulfate, sodium lauryl ether sulfate, and ammonium lauryl sulfate.

4. The composition according to claim 1, wherein the moisturizing agent is selected from the group consisting of ethylene glycol, propylene glycol, glycerin, sorbitol, low molecular weight polyethylenes, polyoxyethylated glycerols, and polyoxyethylated sugars.

5. The composition according to claim 1, wherein the solvent is selected from water and water-hydrosoluble alcohol mixtures.

6. A method for removing or reducing acne in a subject in need thereof, the method comprising administering the hydrosoluble topical pharmaceutical composition of claim 1 to skin of the subject.

7. A topical pharmaceutical composition, comprising:
   a) diallyl disulfide modified oxide;
   b) glycolic acid;
   c) a surfactant selected from the group consisting of (i) sodium lauryl sulfate, (ii) sodium lauryl ether sulfate, and (iii) sodium lauryl sulfate and sodium lauryl ether sulfate; and
   d) a moisturizing agent selected from the group consisting of glycerin, ethylene glycol, and sorbitol.

8. The composition of claim 7, wherein the diallyl disulfide modified oxide is 0.8% by weight of the composition.

9. The composition of claim 7, wherein the diallyl disulfide modified oxide is 1.0% by weight of the composition.

10. The composition of claim 7, wherein the moisturizing agent is glycerin.

11. The composition of claim 7, wherein the surfactant is 20% by weight of the composition.

12. The composition of claim 7, wherein the moisturizing agent is 0.4% by weight of the composition.

13. The composition of claim 7, wherein the moisturizing agent is 0.5% by weight of the composition.

14. The composition of claim 7, wherein the glycolic acid is 11.42% by weight or 11.6% by weight of the composition.

15. The composition of claim 1, wherein the composition kills *Propionibacterium acnes*.

16. The composition of claim 7, wherein the composition kills *Propionibacterium acnes*.

* * * * *